US00PP29334P3

(12) United States Plant Patent
Schoone

(10) Patent No.: US PP29,334 P3
(45) Date of Patent: May 29, 2018

(54) ***PHALAENOPSIS* ORCHID PLANT NAMED 'MALIBU BABY'**

(50) Latin Name: *Phalaenopsis hybrida*
Varietal Denomination: Malibu Baby

(71) Applicant: Floricultura, Heemskerk, Netherlands (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 0 days. days.

(21) Appl. No.: 15/330,465

(22) Filed: Sep. 23, 2016

(65) Prior Publication Data

US 2017/0094874 P1 Mar. 30, 2017

Related U.S. Application Data

(60) Provisional application No. 62/222,928, filed on Sep. 24, 2015.

(30) Foreign Application Priority Data

Sep. 28, 2015 (NL) ..... PBR OPS1279

(51) Int. Cl.
*A01H 5/02* (2018.01)

(52) U.S. Cl.
USPC ..... Plt./311

(58) Field of Classification Search
USPC ..... Plt./311
CPC ..... A01H 5/02; A01H 5/00
See application file for complete search history.

(56) References Cited

U.S. PATENT DOCUMENTS

PP24,590 P3 * 7/2014 Schoone ..... A01H 5/02
Plt./311

* cited by examiner

*Primary Examiner* — June Hwu
(74) *Attorney, Agent, or Firm* — Sunit Talapatra; Foley & Lardner LLP

(57) ABSTRACT

A new and distinct *Phalaenopsis* plant named 'Malibu Baby' particularly characterized by flowers which are white with purple/violet in the center of the petals and sepals and also some yellow on the sepals. Labellum is purple/violet, white and yellow; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Malibu Baby'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Malibu Baby'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Malibu Baby' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Malibu Baby' originated from a cross made by the inventor in 2003 in Strengweg, Heemskerk, The Netherlands. The female or seed parent is the *Phalaenopsis* cultivar designated 'Malibu Class', unpatented. The male or pollen parent is the *Phalaenopsis* cultivar designated 'Ying-Yi Scarlet Baby', unpatented. The new *Phalaenopsis* 'Malibu Baby' was discovered and selected by the inventor as a single flowering plant within the progeny of the stated cross in a controlled environment in 2011 in Strengweg, Heemskerk, The Netherlands.

Asexual reproduction of the new *Phalaenopsis* cultivar by tissue culture (mericloning) was first performed in July, 2011 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Malibu Baby', which in combination distinguish this *Phalaenopsis* as a new and distinct cultivar:

1. flowers which are white with purple/violet in the center of the petals and sepals and also some yellow on the sepals. Labellum is purple/violet, white and yellow.
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Malibu Baby', the flowers of the female parent 'Malibu Class' are larger than 'Malibu Baby' with white and yellow in the labellum. The flowers of the male parent 'Ying-Yi Scarlet Baby' are smaller than 'Malibu Baby' and white with purple in color.

Presently, the commercial cultivar to which 'Malibu Baby' can be meaningfully compared is 'Prima Piano' (U.S. Plant Pat. No. 24,590). 'Prima Piano' is white with a fan-shaped violet mark, whereas 'Malibu Baby' is white with a purple/violet mark in the center and some yellow on the sepals.

BRIEF DESCRIPTION OF THE PHOTOGRAPHS

The accompanying photographs illustrate the overall appearance of the new *Phalaenopsis* 'Malibu Baby' showing the colors as true as is reasonably possible with colored reproductions of this type. Colors in the photographs may differ slightly from the color values cited in the detailed botanical description, which accurately describe the color of 'Malibu Baby'.

DETAILED BOTANICAL DESCRIPTION

Figure 1:
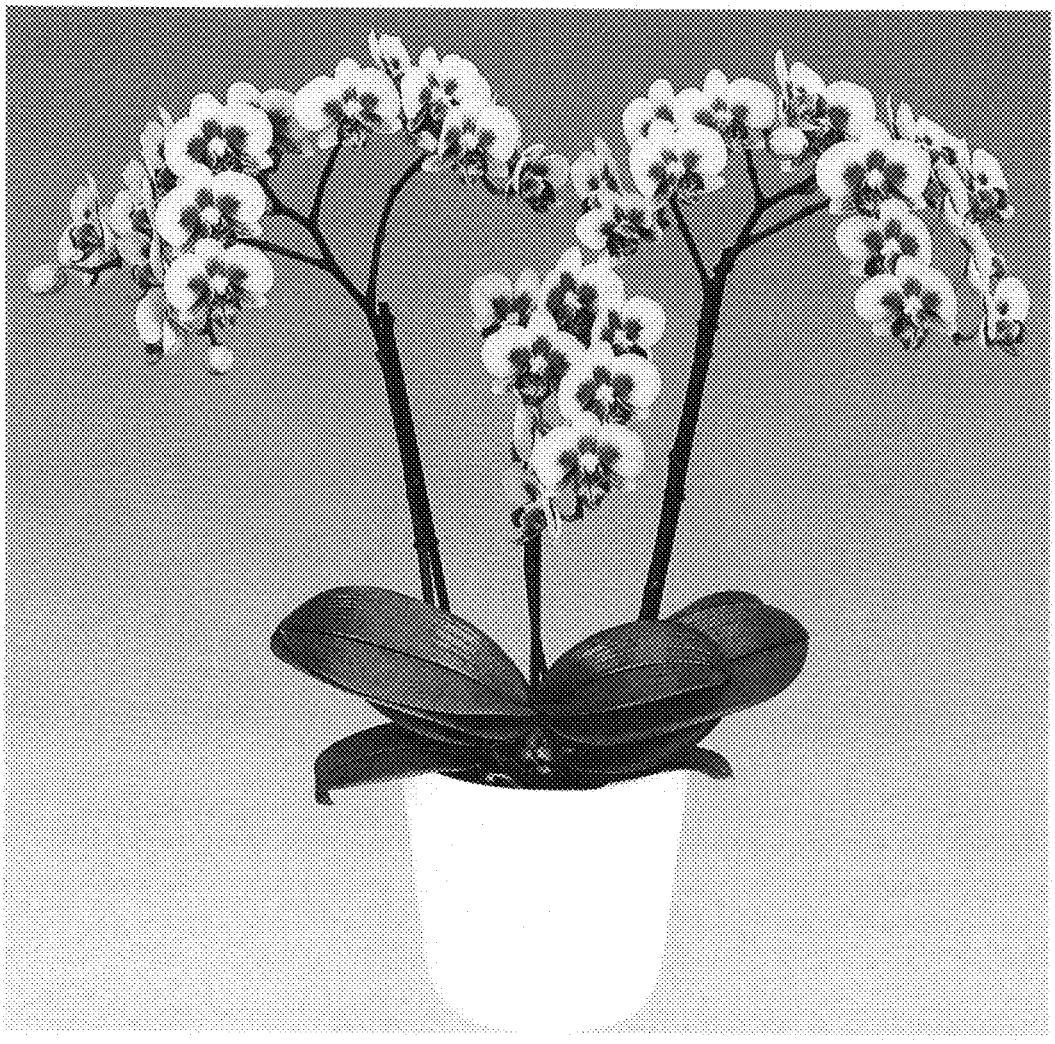
FIG. 1 shows a side view perspective of a typical flowering plant of 'Malibu Baby' in a 12 cm pot, at 16 months of age.

The new *Phalaenopsis* cultivar 'Malibu Baby' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Malibu Baby' as grown in a greenhouse in Strengweg, Heemskerk, The Netherlands, under conditions which closely approximate those generally used in commercial practice. Initially, the ideal temperature to grow plants of 'Malibu Baby' is 27° C. during the day and at night. Then, during the flowering phase of 'Malibu Baby', the ideal growing temperature is 20-22° C. during the day and 18° C. at night. Light levels for growing 'Malibu Baby' are a minimum of 5,000 lux and a maximum of 10,000 lux. A balanced fertilizer with level of 200 ppm N, 87 ppm P, 168 ppm K is applied. Duration of growth of 'Malibu Baby' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Malibu Baby' plants described is 12 months after potting.

Classification:

*Botanical.—Phalaenopsis hybrida.*

Parentage:

*Female or seed parent.—Phalaenopsis* cultivar designated 'Malibu Class', unpatented.

*Male or pollen parent.—Phalaenopsis* cultivar designated 'Ying-Yi Scarlet Baby', unpatented.

Propagation:

*Type.*—Tissue culture.

*Rooting habit and description.*—Fleshy; approximately 3 mm-6 mm wide and greyed/green in color (RHS 190A); freely branching. It takes 12 weeks for plants growing in tissue culture to initiate roots.

Plant:

*Size at maturity.*—Height (from bottom of pot to highest flower): about 30 cm. Spread: about 20-30 cm.

*Growth habit.*—Small; green leaves (RHS N137B) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-3 racemes with flowers appear.

Foliage:

*Quantity per plant.*—About 8 leaves are produced before flowering.

*Arrangement and attachment.*—Alternate, clasping.

*Overall shape of leaf.*—Oval; the tip is blunt and asymmetric.

*Texture (upper & underside).*—Smooth and leathery.

*Pubescence.*—None

*Mature leaf length.*—About 15 cm.

*Mature leaf width.*—About 4 cm.

*Mature leaf thickness.*—About 2 mm.

*Mature leaf color.*—Upper side: green (RHS 137B). Under side: green (RHS 138A).

*Leaf base.*—Acute.

*Margin.*—Entire.

*Venation.*—Pattern: parallel. Color of midvein: upper side: green (RHS N137A) under side: green (RHS N137A).

Inflorescence description:

*Appearance.*—Upright to slightly pendant, racemose inflorescence with bilaterally symmetrical flowers that open in succession beginning with the lowermost flower.

Raceme:

*Quantity per plant*.—About 1 to 3.

*Number of flowers per raceme*.—About 6-18.

*Length*.—About 15 cm.

*Diameter*.—About 10 mm.

Peduncle:

*Length*.—About 25 cm.

*Diameter*.—About 4 mm.

*Strength*.—Strong.

*Aspect*.—Upright.

*Texture*.—Glabrous and smooth.

*Color*.—Green (RHS 143A).

Buds:

*Height* (*from base to tip*).—About 18 mm.

*Diameter* (*at midpoint*).—About 17 mm.

*Shape*.—Asymmetric oval.

*Color*.—Yellow/green (RHS 145C) with red/purple (RHS 70A).

*Orientation*.—Same as flowers (forward facing).

Flowering time: For an untreated plant (flowering plant that has not undergone cold-treatment where the plant grows at a temperature of 18° C. to 19° C. for about 4 to 8 weeks after a period of about 30 weeks at a temperature of 25° C.), 1-3 racemes appear with flower buds and flowers. First flowers can be expected approximately 4 to 6 months after planting a plant with a leaf diameter of 3 to 5 cm. Flowers persistent.

Flowering longevity: On the plant: about 4 to 6 months; lastingness of cut flowers: has not been observed.

Fragrance: No fragrance.

Flower:

*Rate of opening*.—Flowers fully opened about 2 to 3 days after petal and sepal separation.

*Orientation at opening*.—Slanted upward and outward.

Figure 2:
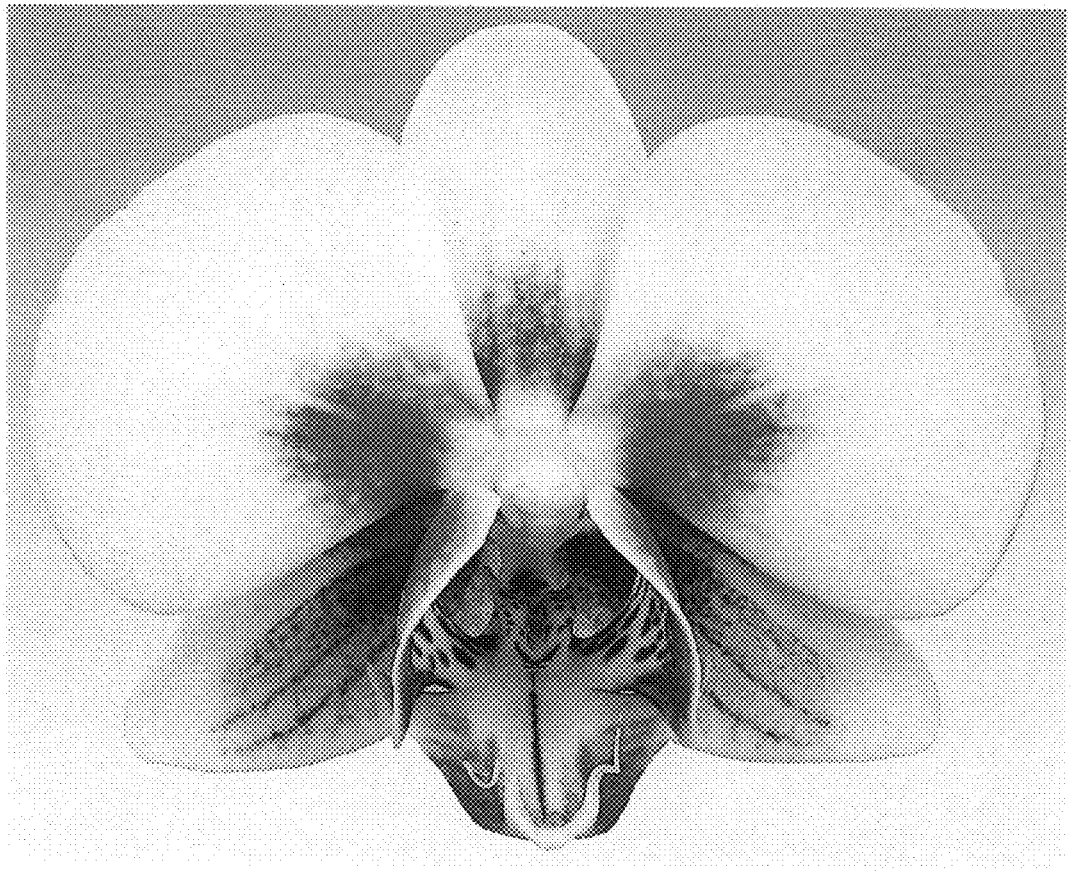
FIG. 2 shows a close-up view of the typical flower of 'Malibu Baby'.
Figure 3:
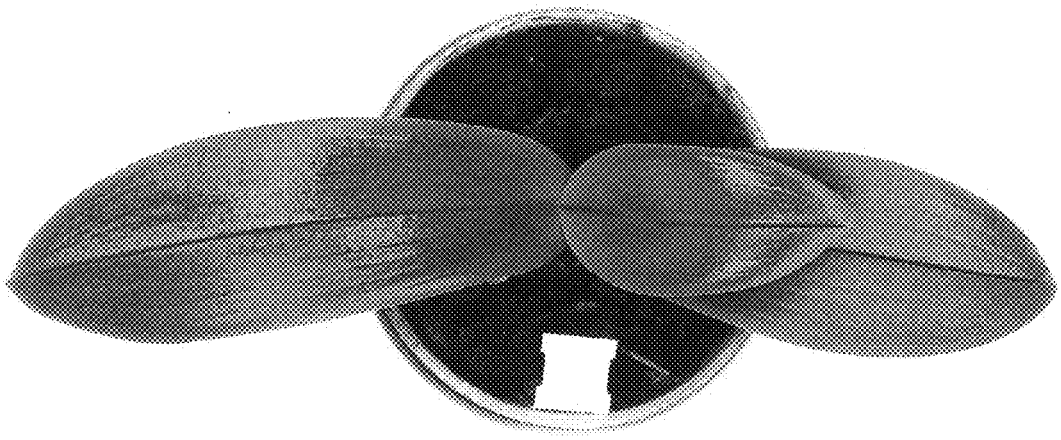
FIG. 3 shows a close-up view of the typical leaves of 'Malibu Baby'.

*Shape*.—Typical shape of *Phalaenopsis*; see FIG. 2.

*Size* (*of single bloom*).—Height: about 5 cm. Diameter: about 6 cm.

*Quantity and arrangement*.—Three petals and three sepals; arrangement of petals are free, not touching. Petals are more pronounced than sepals Petals:

*Arrangement*.—Inner whorl comprises 3 petals: 2 lateral petals and a labellum.

2 *lateral petals*.—Overall shape: little triangular and weakly cupped. Apex: oval. Margin: entire and weakly undulate. Base: broadly ovate. Length: about 25 mm. Width: about 28 mm. Texture: Upper surface: smooth and satiny. Under surface: smooth and satiny. Color (when fully opened): upper side: main color is white (RHS NN155C) with at the base a purple/violet mark (RHS N80A) with some white spots (RHS NN155C and RHS N155B). Under side: main color is white (RHS NN155C) with at the base some purple/violet (RHS N80C). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex of the midlobe and lateral lobes: oval. Length midlobe: about 21 mm. Width midlobe (not flattened): about 20 mm. Length lateral lobe: about 15 mm. Width lateral lobe (not flattened): about 12 mm. Depth of tube created by lateral lobes of labellum: about 15 mm. Texture: Upper & under surface: smooth and satiny. Color (when fully opened): Midlobe, upper side: at the base yellow (RHS 12A) which runs into purple/violet (RHS N80A) with white that appears along the center next to the purple-violet center-stripe (RHSN81A) and from the center towards the apex, with blotches of white around the center and towards the sides of the midlobe (RHS NN155C). Under side: white (RHS NN155C) with in the corners yellow (RHS 12A), and purple/violet on the edges (RHS N80A). Lateral lobes, upper side: at the base white (RHS NN155C) with red/purple stripes and spots (RHS 70A) which runs into purple/violet (RHS N80A) with at the lower edge some yellow (RHS 12A) and the at the upper edge some white (RHS NN155C). Under side: at the base white (RHS NN155C) which runs into purple/violet (RHS N80A). At the bottom edge some yellow (RHS 12A). Cirrhi: about 10 mm. Color: white (NN155C) with speckling of purple/violet (RHS N80B) which runs into yellow (RHS 2D) at the tip. Pestle (Callosities): Length: about 5 mm. Width (not flattened): about 6 mm. Color: white on the sides (RHS NN155C) and yellow on the edges and on the top (RHS 12A) with red/purple stripes and spots (RHS 70A).

Sepals:

*Arrangement*.—Outer whorl comprises 3 sepals, one dorsal and two lateral sepals.

*Overall shape*.—Elliptical and weakly cupped.

*Margin*.—Entire and weakly undulate.

*Length*.—About 25 mm.

*Width*.—About 18 mm.

*Apex*.—Oval; lateral are a little pointy.

*Texture*.—Upper and under surface: smooth and satiny.

*Color* (*when fully opened*).—Upper side, dorsal: Main color is white (RHS NN155C) with at the base white which runs into a purple/violet mark (RHS N80A) with white spots (RHS N155B). Lateral: white (RHS NN155C) with a purple/violet mark at the base (RHS N80A). At the lower part a yellow (RHS 12C) haze with purple stripes and spots (RHS N80B). Under side, dorsal: white (RHS NN155C) with haze of purple/violet (RHS N80A). Lateral: white (RHS NN155C) with haze of purple/violet (RHS N80A). At the base some green/yellow (RHS 144C).

Pedicel:

*Length*.—About 20 mm.

*Diameter*.—About 4 mm.

*Texture*.—Glabrous and smooth.

*Color*.—At the flower white (RHS NN155C) which runs into yellow/green (RHS 144C and RHS 144A).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed to date.

Column:

*Length*.—About 8 mm.

*Diameter*.—About 4 mm.

*Color*.—White (RHS NN155C) and some purple/violet (RHS N80A) stripes and spots.

Pollinia:

*Quantity*.—Two.

*Diameter*.—About 2 mm.

*Color*.—Yellow/orange (RHS 23A).

Ovary:

*Length*.—About 3 mm.

*Diameter*.—About 2 mm.

*Color*.—White (RHS NN155C) with purple/violet on the edges (RHS N80A).

Disease/pest resistance/ susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Malibu Baby', as illustrated and described herein.

* * * * *